(12) United States Patent
Oster et al.

(10) Patent No.: US 6,599,518 B2
(45) Date of Patent: Jul. 29, 2003

(54) SOLVENT DEHYDRATED MICROBIALLY-DERIVED CELLULOSE FOR IN VIVO IMPLANTATION

(75) Inventors: Gerry Ann Oster, Hatfield, PA (US); Kevin Lentz, Perkasie, PA (US); Kevin Koehler, Keyport, NJ (US); Russell Hoon, Furlong, PA (US); Gonzalo Serafica, Troy, NY (US); Richard Mormino, Round Lake, NY (US)

(73) Assignee: Xylos Corporation, Langhorne, PA (US)

( * ) Notice: Subject to any disclaimer, the term of this patent is extended or adjusted under 35 U.S.C. 154(b) by 0 days.

(21) Appl. No.: 09/989,297

(22) Filed: Nov. 21, 2001

(65) Prior Publication Data

US 2002/0107223 A1 Aug. 8, 2002

Related U.S. Application Data

(60) Provisional application No. 60/252,087, filed on Nov. 21, 2000.

(51) Int. Cl.$^7$ .................... A61F 2/02; A61K 31/717
(52) U.S. Cl. .................. 424/425; 523/113; 523/114; 514/57; 536/56
(58) Field of Search ................ 424/423, 425; 514/57; 536/56; 162/99; 523/113, 114

(56) References Cited

U.S. PATENT DOCUMENTS 5,846,213 A  * 12/1998  Wan ..................... 602/49

* cited by examiner

Primary Examiner—Carlos A. Azpuru
(74) Attorney, Agent, or Firm—Foley & Lardner

(57) ABSTRACT

A solvent dehydrated microbially-derived cellulose material is described for use as an implantable material in general and plastic surgery.

17 Claims, 18 Drawing Sheets

SDMC
Tensile Strength

SDMC
Tensile Strength & % Elongation

SOLVENT DEHYDRATED MICROBIALLY-DERIVED CELLULOSE FOR IN VIVO IMPLANTATION

This application claims the benefit of provisional application No. 60/252,087, filed Nov. 21, 2000.

FIELD OF THE INVENTION

This invention relates to polysaccharide materials and more particularly to microbially derived cellulose having suitable implantation properties for medical and surgical applications. The invention also relates to use of the microbially derived cellulose as tissue repair materials, human tissue substitutes and bulking agents for plastic and reconstructive surgery.

BACKGROUND OF THE INVENTION

The widespread use of synthetic materials as implantable devices in the medical industry has been well documented. These implantable synthetic materials can generally be divided into two major groups, temporary/bioresorbable and long-term implants/non-biodegradable. Examples of bioresorbable synthetic materials include polymers comprising polylactic (PLA) and polyglycolic acid (PGA), which have long been used as surgical sutures. These materials have been fabricated into films, mesh and more complex three-dimensional structures depending on intended applications as described in U.S. Pat. No. 6,031,148.

An example of long-term implantable and non-biodegradable materials is poly(tetrafluoroethylene) PTFE, which has been used in wide array of medical implantable articles including vascular grafts (U.S. Pat. No. 5,718,973), tissue repair sheets and patches (U.S. Pat. No. 5,433,996). Polymeric hydrogels have also been adapted for surgical implants (U.S. Pat. No. 4,836,884), finding uses such as soft tissue and blood vessel substitutes.

Each of these materials possesses certain physical characteristics that make them suitable as implant materials. Such properties include good biocompatibility, strength, chemically stability, etc. which can be particularly important for a specific application. For example, PTFE has the strength and ability for interconnecting fibril structure that is critical in fabrication of tubular grafts. Synthetic hydrogels, which have a superficial resemblance to living tissue due to high water content, display minimal irritation to surrounding tissues making them ideal as prosthetic devices. However, these synthetic materials also have limitations and disadvantages such as a limited range of physical and biochemical properties. Thus, there remains a need to explore alternative materials more suitable for specific surgical applications.

The use of viscose or regenerated cellulose as implantable articles is known. Several investigators have studied tissue biocompatibility of cellulose and its derivatives (Miyamoto, T. et. al., *Tissue Biocompatibility of Cellulose and its derivatives. J. Biomed. Mat. Res.,* V. 23, 125–133 (1989)) as well as examined some specific applications for the material. The oxidized form of regenerated cellulose has long been used as a hemostatic agent and adhesion barrier (Dimitrijevich, S. D., et. al. *In vivo Degradation of Oxidized regenerated Cellulose. Carbohydrate Research,* V. 198, 331–341 (1990), Dimitrijevich, S. D., et. al. *Biodegradation of Oxidized regenerated Cellulose Carbohydrate Research,* V. 195, 247–256 (1990)) and are known to degrade much faster than the non-oxidized counterpart. A cellulose sponge studied by Martson, et. al., showed sufficient biocompatibility with bone and connective tissue formation during subcutaneous implantation (Martson, M., et. al., *Is Cellulose sponge degradable or stable as an implantation material? An in vivo subcutaneous study in rat. Biomaterials,* V. 20, 1989–1995 (1999), Martson, M., et. al., *Connective Tissue formation in Subcutaneous Cellulose sponge implants in rats. Eur. Surg. Res.,* V. 30, 419–425 (1998), Martson, M., et. al., *Biocompatibility of Cellulose Sponge with Bone. Eur. Surg. Res.,* V. 30, 426–432 (1998)). The authors summarized that the cellulose material can be a viable long-term stable implant. Other forms and derivatives of cellulose have also been investigated (Pajulo, O. et. al. *Viscose cellulose Sponge as an Implantable matrix: Changes in the structure increase production of granulation tissue. J Biomed. Mat. Res.,* V. 32, 439–446 (1996), However, the prior art fails to mention the possible use of a unique form of cellulose produced by certain unicellular organisms. In this regard, microbial cellulose produced by certain microorganisms has been known and studied for over a hundred years. Microbially derived cellulose possesses distinct characteristics not found in plant cellulose, including high water content similar to hydrogels and exceptional strength like PTFE. Microbial cellulose can be synthesized in various shapes or sizes, and has excellent shape retention. These properties are mostly attributed to its unique laminar microfibrillar three-dimensional structure. The microfibrils arranged in a nonwoven manner are about 200 times finer than plant cellulose such as cotton fibers, yielding tremendous surface area per unit volume.

Even with the multitude of novel properties, microbial cellulose has not been fully utilized, and thus, limited applications have been suggested. For example, the use of microbially derived cellulose in the medical industry has been limited to liquid loaded pads (U.S. Pat. No. 4,588,400), wound dressings (U.S. Pat. No. 5,846,213) and other topical applications (U.S. Pat. No. 4,912,049). Mello et al., (Mello, L. R., et. al., *Duraplasty with Biosynthetic Cellulose: An Experimental Study. Journal of Neurosurgery,* V. 86, 143–150 (1997)) published the use of biosynthetic cellulose similar to the one described in (U.S. Pat. No. 4,912,049) as a duraplasty material in an experimental animal study. Their results showed that the dried form of the microbially derived cellulose was adequate as a dural substitute. However, the material described by Mello et al. does not undergo a depyrogenation step and the material is dried while being stretched as described in U.S. Pat. No. 4,912,049. In contrast, the instant invention provides a non-pyrogenic implantable material and uses a variety of drying methods such as solvent dehydration.

In another aspect of the invention, various methods have been described in drying microbial cellulose. Blaney et al. in U.S. Pat. Nos. 5,580,348 and 5,772,646 describe an absorbent material which comprises a microbial polysaccharide having a mean pore size of about 0.1 to about 10 microns. The absorbent material is prepared by a process that comprises supercritical drying of a microbial polysaccharide to remove at least a portion of the aqueous medium that is present when the microbial polysaccharide is produced.

The product and process of Blaney et al. differ from the present product and process discovered by the present inventors, the present inventors have determined a method of preparing implantable microbial cellulose by dehydrating the microbially-derived cellulose with a water-miscible solvent such as methanol, ethanol, propanol, isopropanol, acetone and mixtures thereof. The product of Blaney et al. also differs from the present product in that the present product is capable of in vivo implantation as a result of non-pyrogenicity (non-endotoxicity), enhanced tensile strength and suture retention, sterilization by gamma irradiation, and biocompatibility.

A product that is similar to the material described in the present invention is the material of U.S. Pat. No. 4,912,049. As mentioned previously, the prior art describes a process of dehydrating microbial cellulose while being stretched. The prior art material has been used for various medical applications including wound dressing and implanted as a dura substitute. However, in comparison to the present invention, the material known as BIOFILL™ lacks the strength and sutureability characteristics to be useful as an implantable surgical mesh.

Thus, prior to the present invention there has not been an acceptable implantable material comprising microbially-derived cellulose. Accordingly, there remains a need for an implantable material comprising microbially derived cellulose that can be used for a wide variety of medical and surgical applications. Methods of implanting a microbially-derived cellulose for a variety of applications are also particularly desirable.

OBJECTIVES OF THE INVENTION

An object of the present invention is to provide a microbially-derived implantable cellulose, wherein the material is capable of in vivo implantation, and the method for producing the same. The material can be used as a tissue substitute, bulking agent and a surgical mesh. Another object of the invention is to provide microbially-derived implantable cellulose, wherein the material is capable of in vivo implantation, that has desirable mechanical properties such as tensile strength, elongation and sutureability. Still another object of the invention is to provide a microbially derived cellulose that is non-pyrogenic and biocompatible and is capable of being sterilized. These and other objectives will readily become apparent to those skilled in the art in view of the teachings hereinafter set forth.

SUMMARY OF THE INVENTION

Figure 1:
FIG. 1 shows mechanical strength with a typical stress-strain curve of the solvent dehydrated microbially derived cellulose after re-hydration.

The materials of the present invention comprise an implantable form of solvent dehydrated microbially-derived cellulose, particularly cellulose produced from cultures of *Acetobacter xylinum* propagated in a nutrient media and incubated under controlled conditions. The cellulose film or pellicle is produced via *A. xylinum* propagation inclusive of incubation under controlled conditions. The pellicle is chemically treated with sodium hydroxide to destroy pyrogens and viable microorganisms then the pellicle is bleached with hydrogen peroxide to whiten the cellulose. Following compression of each pellicle, the material is treated with a water-miscible organic solvent such as acetone for several cycles to optimize dehydration. The material is then again compressed, undergoes a final drying step, is cut and packaged, and gamma sterilized.

In one aspect of the invention, there is provided a method for producing solvent dehydrated cellulose from microbially derived cellulose. The method comprises the steps of propagating cellulose-producing microbes in a nutrient media under controlled conditions followed chemically treating the microbially-derived cellulose with sodium hydroxide to depyrogenate the material and destroy viable organisms, followed by bleaching the microbially-derived cellulose with hydrogen peroxide to whiten the cellulose prior to further processing.

In another aspect of the invention, the cellulose is dehydrated (water is removed) by processing the cellulose with a water-miscible organic solvent selected from the group consisting of methanol, ethanol, propanol, isopropanol, acetone and mixtures thereof.

In a further aspect of the invention the solvent dehydrated microbially-derived cellulose is used as an implantable medical material for plastic and general surgery. The solvent dehydrated microbially-derived cellulose is useful in general and plastic surgery because it can be cut into desirable sizes and shapes to meet surgical requirements.

A further aspect of the invention relates to a kit comprising microbially-derived cellulose and a package comprising a sealed waterproof pouch, optionally placed within a secondary waterproof pouch, and gamma sterilized.

DETAILED DESCRIPTION OF THE INVENTION

In preparing the solvent dehydrated microbially-derived cellulose (SDMC) of the present invention, the cellulose was synthesized by a bacteria, preferably the bacteria *Acetobacter xylinum* (wild type), and was recovered from inoculation flasks and propagated via continued inoculation and incubation for linear growth in subsequent flasks and carboys of optimized media to attain the desired volume of microbially derived cellulose. The media is comprised of nutrients such as sucrose, ammonium sulfate, sodium phosphate, magnesium sulfate, citric acid, acetic acid and trace elements resulting in a growth media having a pH of about 4.0 to about 4.4. The sterilized media is inoculated from propagation cultures of *A. xylinum* and filled into bioreactor trays at the appropriate volume to yield the a final cellulose to water ratio of about 90% to 95% water to about 5% to 10% cellulose. The bioreactor trays are sealed and incubated in a controlled environment at 30° C.±2° until growth of a pellicle of microbially-derived cellulose is complete. The pellicles are removed from the bioreactor trays and are chemically treated to remove bacterial by-products and residual media. A caustic solution, preferably sodium hydroxide at a preferable concentration of about 0.1M to 4M, is used to remove viable organisms and pyrogens (endotoxins) produced by bacteria from the pellicle. The treated pellicles are then rinsed with filtered water to reduce microbial contamination (bioburden). The chemically processed cellulose films (pellicles) are then exposed to a "bleaching" process to attain a "whitening" effect on the material. A typical bleaching solution of hydrogen peroxide is in the range of about 0.25% to about 3% and is prepared from concentrated hydrogen peroxide and filtered water.

In a controlled environment, the pellicles are compressed to the desired thickness. It is the thickness of the compressed film that achieves the final desired density of the microbially-derived cellulose. The original fill volume as well as the compression steps are integral to the present invention to attain the desired density that affects the strength, integrity, and function of the cellulose. Further processing of the present invention continues with the use of a water-miscible organic solvent selected from the group consisting of methanol, ethanol, propanol, isopropanol, acetone and mixtures thereof to dehydrate the cellulose. Without being bound to any one theory, it is believed that soaking the compressed films in a water-miscible organic solvent cross-links the cellulose fibers, thereby yielding a product having increased tensile strength, reduced elongation (stretch) and increased suture retention when used as an implantable medical device for various surgical procedures. Depending on the desired level of dehydration, the solvent treated films are exposed to one or more applications of the organic solvent then the films are subsequently compressed to the desired thickness in a controlled environment. The solvent is removed by either air-drying at ambient temperature or oven-drying at about 30° C. under controlled conditions. Dried samples are tested on a residual moisture balance as confirmation of the desired residual moisture of less than about 15%.

In a controlled environment, the films can be cut to various shapes and sizes that those skilled in the art will understand. It is possible for each unit to be packaged in a waterproof double-pouch system and sterilized by exposure to gamma irradiation at a dose level as high as 35 kGy, but preferably a lower dose would be used. The gamma dose is determined by the bioburden level of the non-sterile material as described in ISO 11137 Sterilization of Health Care Products—Requirements for validation and routine control—Radiation Sterilization.

The waterproof packaging is comprised of waterproof inner and outer chevron peelable pouches. The material is a polyester/LDPE/foil blend sealed to silica coated polyester, suitable for sterilization, by, for example gamma irradiation.

The inventive microbially-derived cellulose can be used in tissue augmentation which involves implantation of the subject microbially-derived cellulose material for general as well as plastic surgery applications. Examples of general and plastic surgical uses include but are not limited to, general soft tissue augmentation, pelvic floor reconstruction, bladder neck suspension, hernia repair, inguinal hernia patch and duraplasty.

Another use of the present inventive cellulose material involves their application in sutures. Suture retention is critical for implantable medical articles to secure and maintain position during surgery, healing and function. The surgeon must rely on the ability of the implantable material to not only accept suture without tearing during needle insertion, but to also retain the suture without tearing away from the sutured edge of the implant.

The ability of the present inventive microbially-derived cellulose to be used in surgical procedures requires that the material is safe and effective for its intended purpose and achieves sufficient biocompatibility.

The ability of the present invention to withstand depyrogenation and sterilization processes is necessary toward producing an implantable medical device for general and plastic surgery. Often, biomedical polymers have lower thermal and chemical stability than other materials such as metals, ceramics and synthetics; therefore, they are more difficult to sterilize using conventional methods. For any material used as an implantable medical device, it must be free from endotoxins (non-pyrogenic), microorganisms and other possible contaminants that will interfere with the healing process and cause harm to the recipient.

The present invention undergoes depyrogenation by using a heated caustic solution (0.1M to 4M sodium hydroxide) known to destroy endotoxins that may be present due to bacteria or cross-contamination from materials exposed to pyrogens. The material is then gamma irradiated at doses sufficient to destroy microorganism contamination by predetermined sterility assurance levels based on bioburden levels (the amount of microorganisms typically present on the non-sterile material.) Samples were gamma irradiated at a dose of about 35 kGy. It can be concluded that the material can be depyrogenated with a strong alkaline sodium hydroxide solution at an elevated temperature and that it can withstand gamma sterilization without any significant affect to mechanical properties.

Medical devices intended for implant must meet vorious criteria to comply with either U.S. Food and Drug Administration (FDA) regulations or the International Organization for Standardization (ISO) requirements in order to be deemed fit for their intended use. Cytotoxicity studies are considered relevant to prove that the implant device is safe/biocompatible with human tissue. In vitro biocompatibility studies, based on the International Organization for Standardization 10993: Biological Evaluation of Medical Devices, Part 5: Tests for Cytotoxicity: in vitro Methods guidelines, were conducted on the present invention to determine the potential for cytotoxicity.

The mechanical properties of the microbially-derived cellulose relates to tensile strength, % elongation and suture retention. The material is considered multidirectional as well as possessing the properties of a linear polymer whereas the polymer chains tend to line up in the direction of draw; therefore no regard was made for the direction of the cutting.

The following examples are given to illustrate the present invention. It should be understood, however, that the invention is not to be limited to the specific conditions or details described in these examples. Throughout the specification, any and all references are specifically incorporated into this patent application by reference.

EXAMPLE 1

Manufacture of Implantable Microbially-Derived Cellulose

This example is directed to a preparation of standard solvent dehydrated microbially-derived cellulose films produced by *A. xylinum* within a controlled environment to minimize bioburden (microorganism contamination.) From a propagation vessel, sterilized media was inoculated with *A. xylinum,* filled into bioreactor trays at a volume of about 180 g, and incubated for 10 days when optimal growth of the pellicle was observed. The pellicles were extracted from the trays and then underwent chemical processing (depyrogenation) in a tank of 8% sodium hydroxide which was heated to about 90° C. to 95° C. for about one hour. The pellicles then underwent a continuous rinse with filtered water until the pH was below 10.0. The material was treated with 0.25% hydrogen peroxide at 44° C. to 45° C. for about 30 minutes when the films were observed to be adequately bleached. The films were then rinsed with filtered water until the hydrogen peroxide level was below 1000 ppm. The films were compressed within a pneumatic press to yield a pellicle having a thickness of approximately 2 mm, water content on the order of 95%, and microbially-derived cellulose content approaching 5%.

The pressed films subsequently underwent solvent dehydration treatment with acetone, with daily changes of fresh acetone over the course of 5 days to achieve optimum dehydration. The films were again compressed within a pneumatic press to about 0.2 mm and stacked on trays for drying in a safety oven. The material was dried at about 30° C. for no more than 24 hours. The films were removed from the oven and cut into various sizes and shapes. The excess material was assayed for residual moisture. The residual moisture for the batch was less than 10%. Each unit was placed in an "inner" pouch, sealed, then placed within an "outer" pouch and sealed. The pouches were then sterilized via gamma irradiation at a dose in the range of 3.5 kGy. The sterilized samples made in accordance with the present invention were used for various tests, inclusive of tensile strength, elongation, and suture retention (pull-out).

EXAMPLE 2

Manufacture of Solvent Dehydrated Microbially-Derived Films of Varying Thicknesses Thin (0.5× standard) and thick (2× standard) solvent dehydrated microbially-derived cellulose films produced by *A. xylinum* were prepared generally according to the procedure of Example 1

From a propagation vessel, sterilized media was inoculated with *A. xylinum,* filled into bioreactor trays at two different volumes of approximately 90 g and 360 g respectively, and incubated until optimal growth of the pellicle was observed. The pellicles were extracted from the trays and then underwent chemical processing (depyrogenation) in a tank of 8% sodium hydroxide which was heated to about 90° C. to 95° C. for about one hour. The pellicles then underwent a continuous rinse with filtered water until the pH was below 10.0. The material was treated with 0.25% hydrogen peroxide at 44° C. to 45° C. for about 30 minutes when the films were observed to be adequately bleached. The films were then rinsed with filtered water until the hydrogen peroxide level was below 1000 ppm. The films were compressed within a pneumatic press to yield a pellicle having a thickness of approximately 1 mm and 3 mm respectively, water content on the order of 95%, and microbially-derived cellulose content approaching 5%.

The pressed films subsequently underwent treatment with acetone, with daily changes of fresh acetone over the course of 5 days to achieve optimum dehydration. The films were again compressed within a pneumatic press to about 0.05 mm and 1.0 mm respectively and stacked on trays for drying in a safety oven. The material was air-dried at about 30° C. for no more than 24 hours. The films were removed from the oven and cut into various sizes and shapes. The excess material was assayed for residual moisture. The residual moisture for both the thin and thick units within the batch was less than 10%. Each unit was placed in an "inner" pouch, sealed, then placed within an "outer" pouch and sealed. The pouches were then sterilized via gamma irradiation at a dose in the range of 3.5 kGy. The sterilized samples made in accordance with the present invention were used for various tests, inclusive of tensile strength, elongation, and suture retention (pull-out).

EXAMPLE 3

Mechanical Properties Of Solvent Dehydrated Microbially-Derived Cellulose Films A. Testing of Mechanical Properties of Microbially-Derived Cellulose Mechanical tests of the subject solvent dehydrated microbially-derived cellulose were performed to determine the tensile strength, elongation, and suture retention (pull-out) as applicable for an implantable medical material. Samples from the present invention were cut into 1 cm×4 cm strips for testing, using surgical scissors and a template. For example, each strip was not cut from an area parallel to the edge of the film, but strips were cut from various directions within the film to represent the overall area within each film. The thickness was measured using electronic calipers in millimeters, accurate to ±0.03 mm.

The mechanical properties of the solvent dehydrated microbially-derived cellulose were determined using a tensile machine (United Calibration Corporation) Model SSTM-1-PC with a load versus crosshead distance traveled setup. The 1000 lb. load cell was calibrated. The gauge length of the specimen was recorded before the start of each test. The gauge length is the length of the specimen between each grip (determined as 25 mm for each 40 mm strip and 60 mm for each strip with sutures attached.) The top grip was smooth aluminum mounted on a swivel joint to assure alignment with the bottom grip. The bottom grip was smooth steel, secured within the machine base to avoid motion during each pull cycle. Two setscrews were used to unilaterally tighten the sample within the clamps of each grip. Each sample was presented before testing to ensure that the sample was straight and the load was zero. The preload was set at 5 mm/minute and the crosshead speed set at 300 mm/minute.

Each sample was re-hydrated for no less than 10 minutes in filtered water. For tensile strength and elongation testing, each sample was centrally positioned in the top clamp of the testing machine so that the long dimension was parallel to the direction of the force application. The top grip was tightened via setscrews to equally distribute the holding pressure along the surface. The bottom of the sample was positioned in the bottom clamp and tightened via setscrews. For suture retention, each sample was prepared by inserting 2 sutures into one end of the test sample, 2 mm from the end and 3 mm from each edge. Ethicon 2-0 Prolene Suture was used with a taper SH needle. The top grip was tightened via setscrews to equally distribute the holding pressure along the surface. The sutures were carefully inserted between the clamps of the lower grip, parallel to the direction of the force application, and tightened. The swivel joint allowed samples to remain even and parallel to the direction of the force application. A mark was made across the sample at the front inner edge of each grip to check for sample slippage. A guideline was followed whereas if a sample slipped in the clamps, or breaks at the edge of or in the clamps, or the sample breaks and the suture is not torn from the sample, or if for any reason the result falls markedly below the average of the set of samples, the result was discarded and the test repeated pending availability of material. Results in a value below 50% of the average of all other breaks or tears were discarded.

Samples were tested at a constant rate of 300 mm/minute until the sample broke or until the suture material tore through the sample. The ultimate tensile strength (stress at failure) and percent elongation (maximum strain) were calculated from the stress-strain curves generated by the tensile machine software.

B. Results of Tensile Strength and % Elongation Tests

Figure 2:
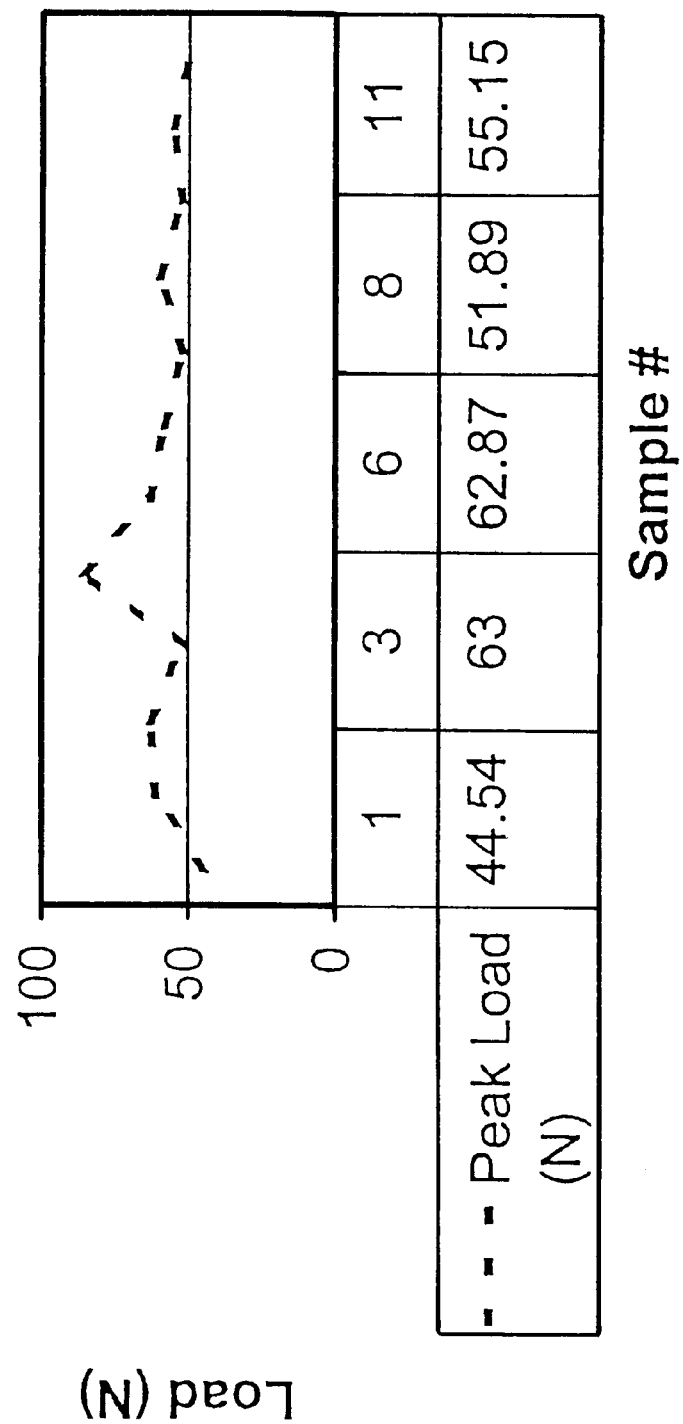
FIG. 2 shows mechanical strength of tensile strength of 12 solvent dehydrated microbially derived cellulose samples after re-hydration.
Figure 3:
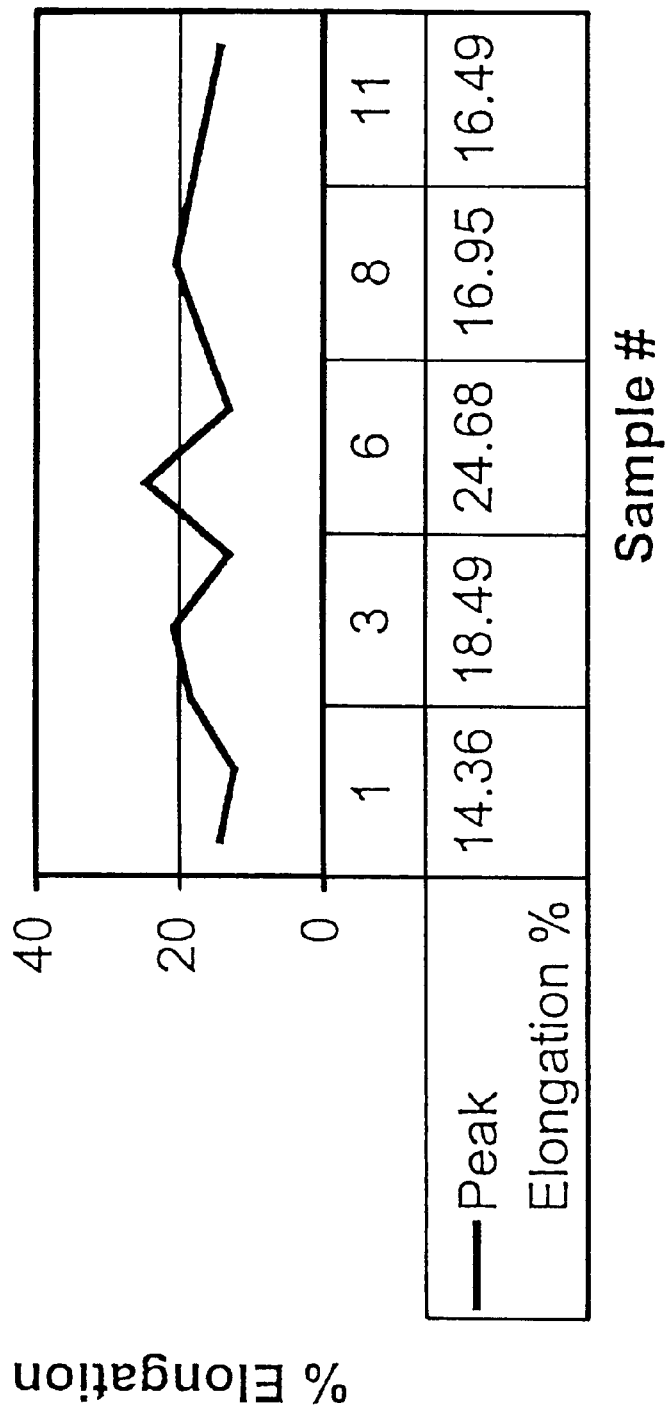
FIG. 3 shows mechanical strength of % elongation from 12 solvent dehydrated microbially derived cellulose samples after re-hydration.
Figure 4:
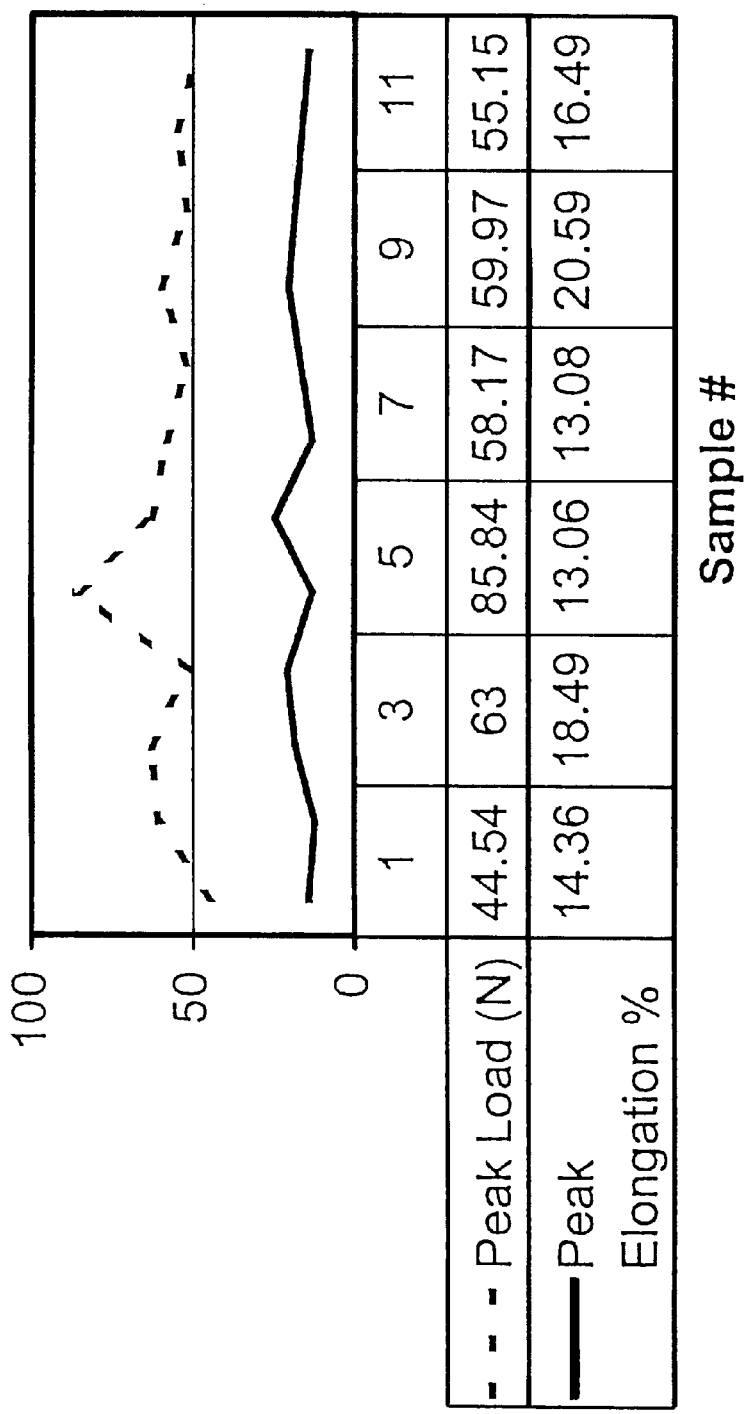
FIG. 4 shows mechanical strength of tensile strength and % elongation of 12 solvent dehydrated microbially derived cellulose samples after re-hydration.

A typical stress-strain curve of the solvent dehydrated microbially-derived cellulose after re-hydration is shown in FIG. 1. The tensile strength of 12 samples is shown in FIG. 2 and the % elongation from 12 samples is shown in FIG. 3. The 12 samples were prepared according to the procedure of example 1. FIG. 4 shows the combined tensile strength and % elongation of the 12 samples.

Table 1 shows an average of the testing where the Peak Load (lbs) which was converted to Peak Load (Newtons) and the % Elongation was calculated as the maximum strain versus stress from each respective stress-strain curve. All samples fell within the inventor's Standard Operating Procedure TST005 Determination of Tensile Strength and Elongation of Solvent Dehydrated Microbial Cellulose—Strip Method guideline to discard any break occurring within 2 mm of the grips which resulted in a value below 50% of the average of all other breaks All results were valid.

| Solvent Dehydrated Microbially-Derived Cellulose | | |
|---|---|---|
| Peak Load (N) | Peak Load (kN) | Peak Elongation % |
| 57.25851957 | 0.057259 | 16.78446077 |

The tensile strength ranged from 45 to 86 Newtons, falling within the 50% discard guideline for determination of consistent, reliable results when testing a biological material. The % Elongation ranged from 12% to 25%. These values indicate the expected low degree of stretch when implantable material is used to support or retain soft tissue repair during general and plastic surgery. It is believed that the polymer organization in wet cellulose is loosely aligned; however, drying allows the polymer chains to become more organized, leading to an increase in strength and a decrease in fracture strain. This becomes apparent as solvent dehydrated microbially-derived cellulose presents the lowest strain to fracture and the highest elastic modulus when compared to wet microbially-derived cellulose.

EXAMPLE 4

Suture Retention

Figure 5:
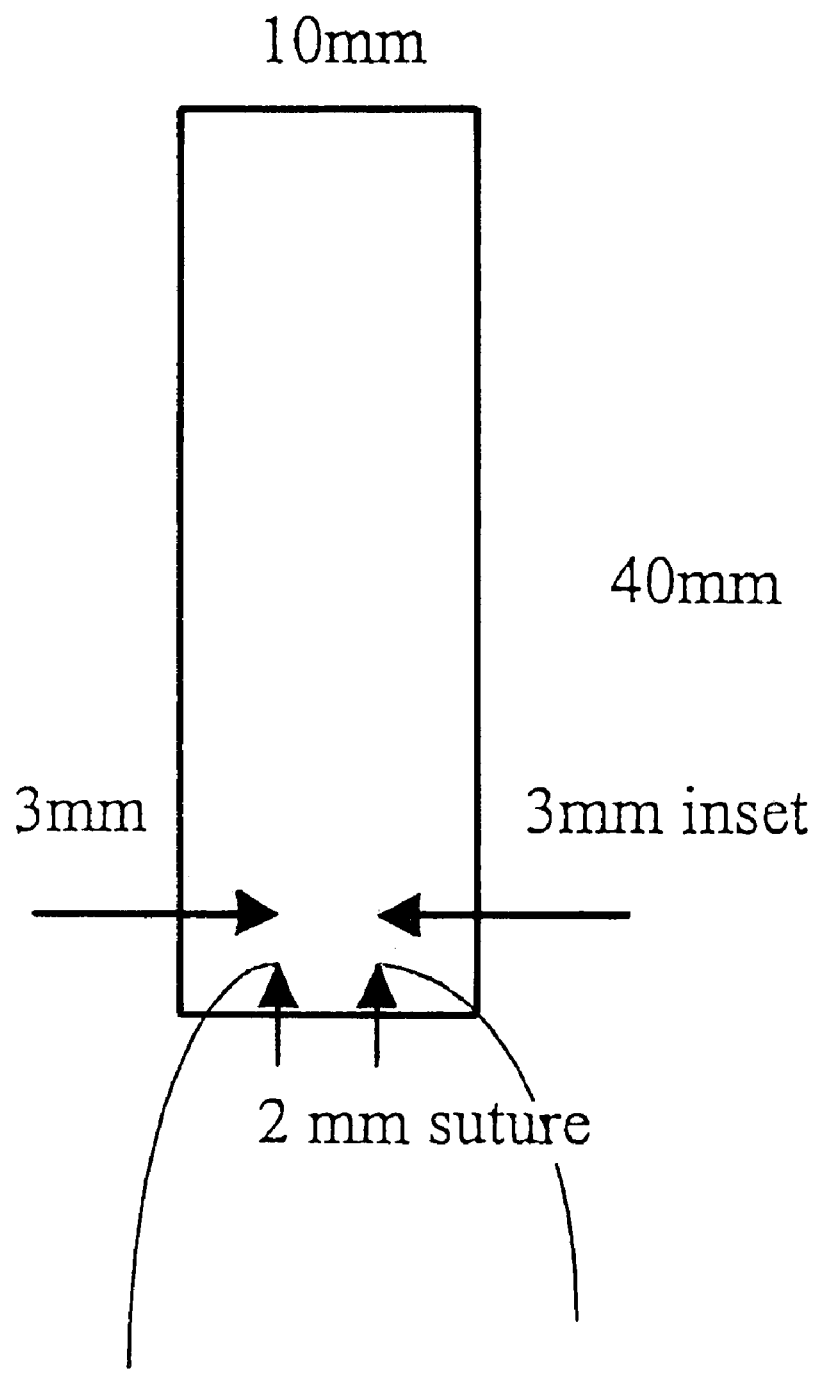
FIG. 5 shows a diagram of placement of suture in solvent dehydrated microbially-derived cellulose sample after re-hydration.

Instructions for suturing commercial products typically require suturing no less than 2 mm from the edge of the product to the soft tissue at the surgical site; therefore all samples were tested by inserting the suture 2 mm from the bottom edge and 3 mm from the side of the sample (See FIG. 5). It is necessary to examine suture pull-out data when comparing to other materials and commercial products to determine fundamental performance.

Figure 6:
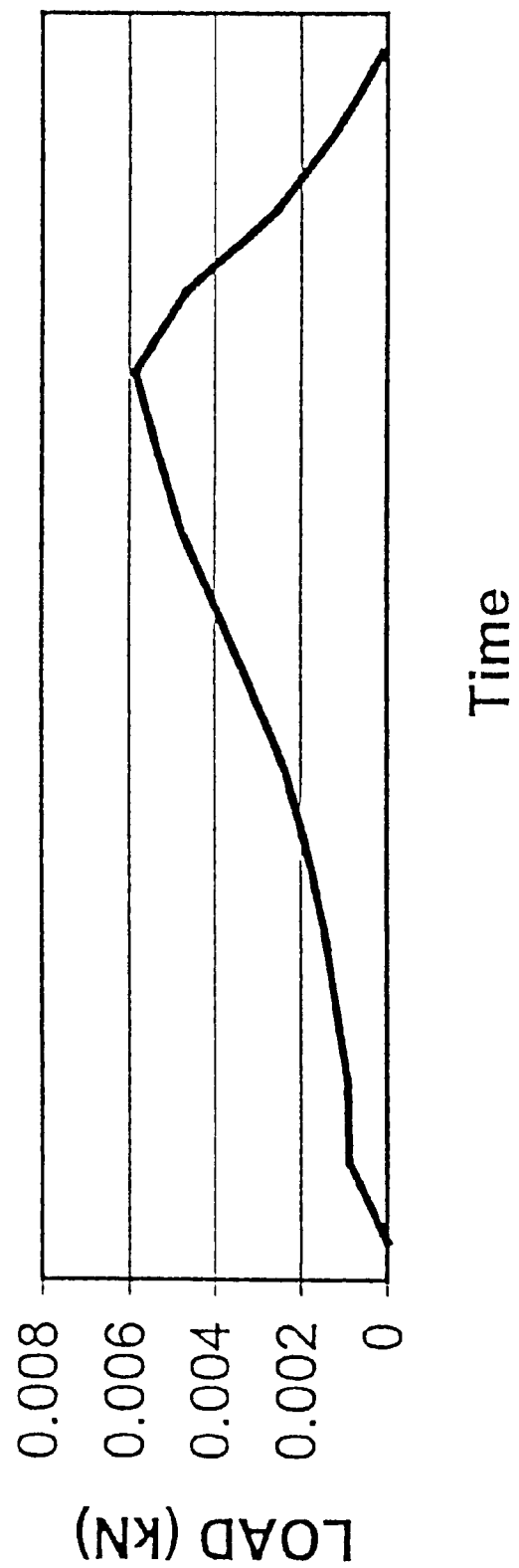
FIG. 6 shows suture retention of a typical stress-strain curve of solvent dehydrated microbially derived cellulose after re-hydration and suture retention testing.
Figure 7:
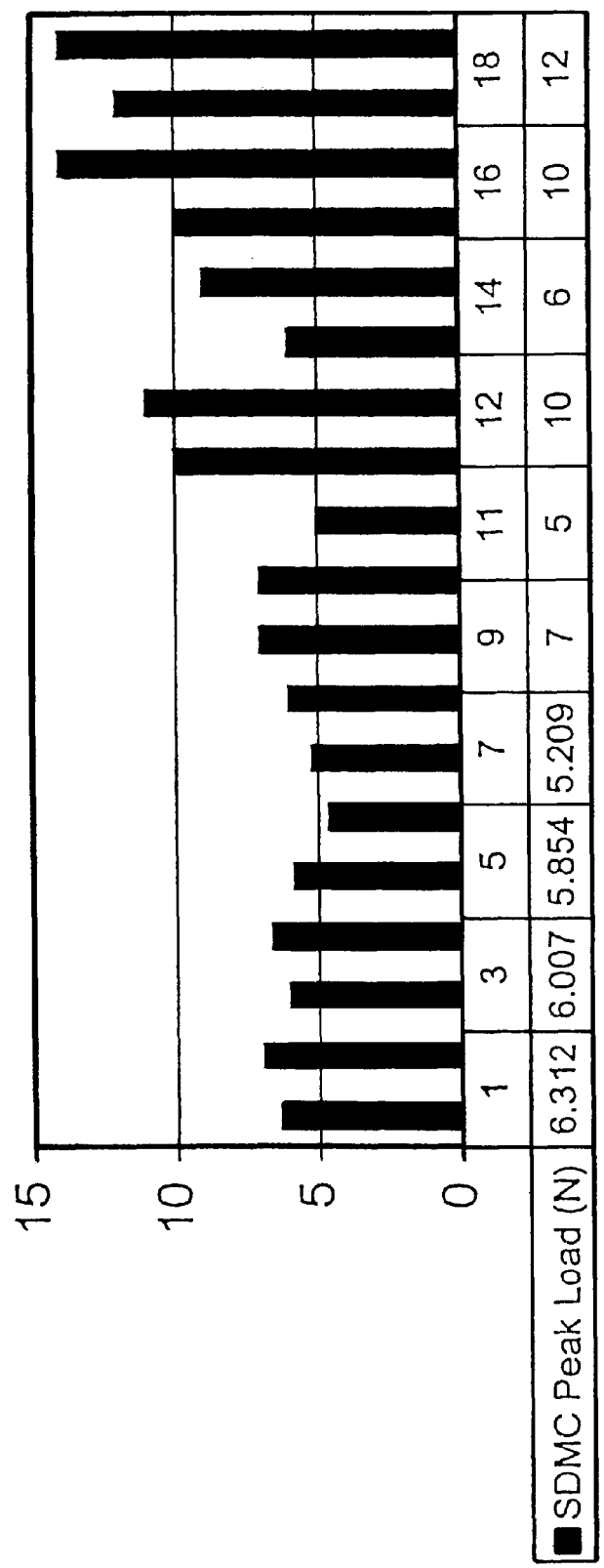
FIG. 7 shows suture retention of results of solvent dehydrated microbially derived cellulose after re-hydration and testing of nineteen samples.

A typical stress-strain curve of the present invention after re-hydration and suture retention testing is shown in FIG. 6.

Table 2 shows testing results where the Peak Load (lbs) was converted to Peak Load (Newtons). There were nineteen samples which fell within the inventor's Standard Operating Procedure TST006 Determination of Suture Retention (Pullout) Strength of Solvent Dehydrated Microbial Cellulose. This test method instructs the operator to discard any break suture tear which results in a value below 50% of the average of all other suture tears. All results were valid.

TABLE 2

| Average results of Suture Retention |
|---|
| SDMC Average Peak Load (N) |
| 8.030164126 |

EXAMPLE 5

Figure 8:
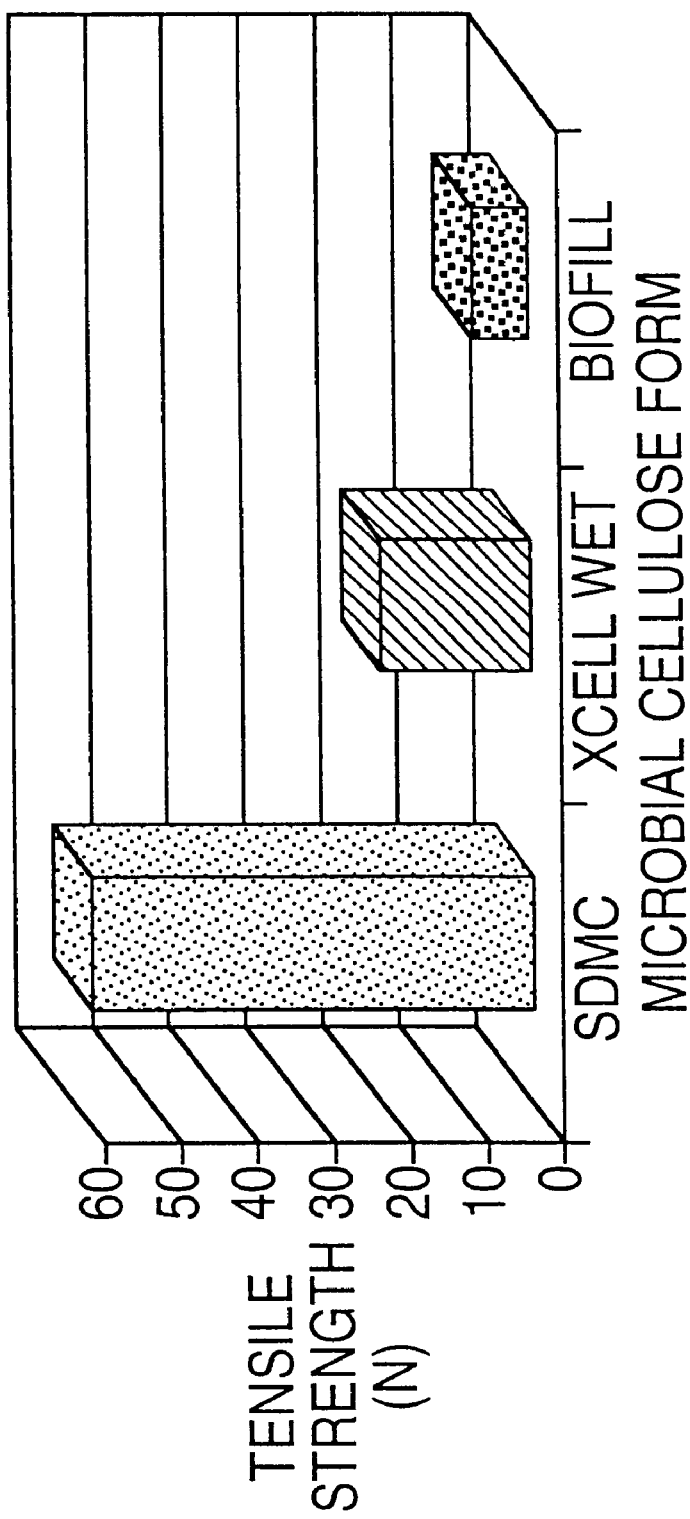
FIG. 8 shows mechanical strength in a graph of comparative data which indicates that solvent dehydrated microbially derived cellulose is superior in tensile strength to wet cellulose (XCELL®) and air-dried cellulose (BIOFILL™).
Figure 9:
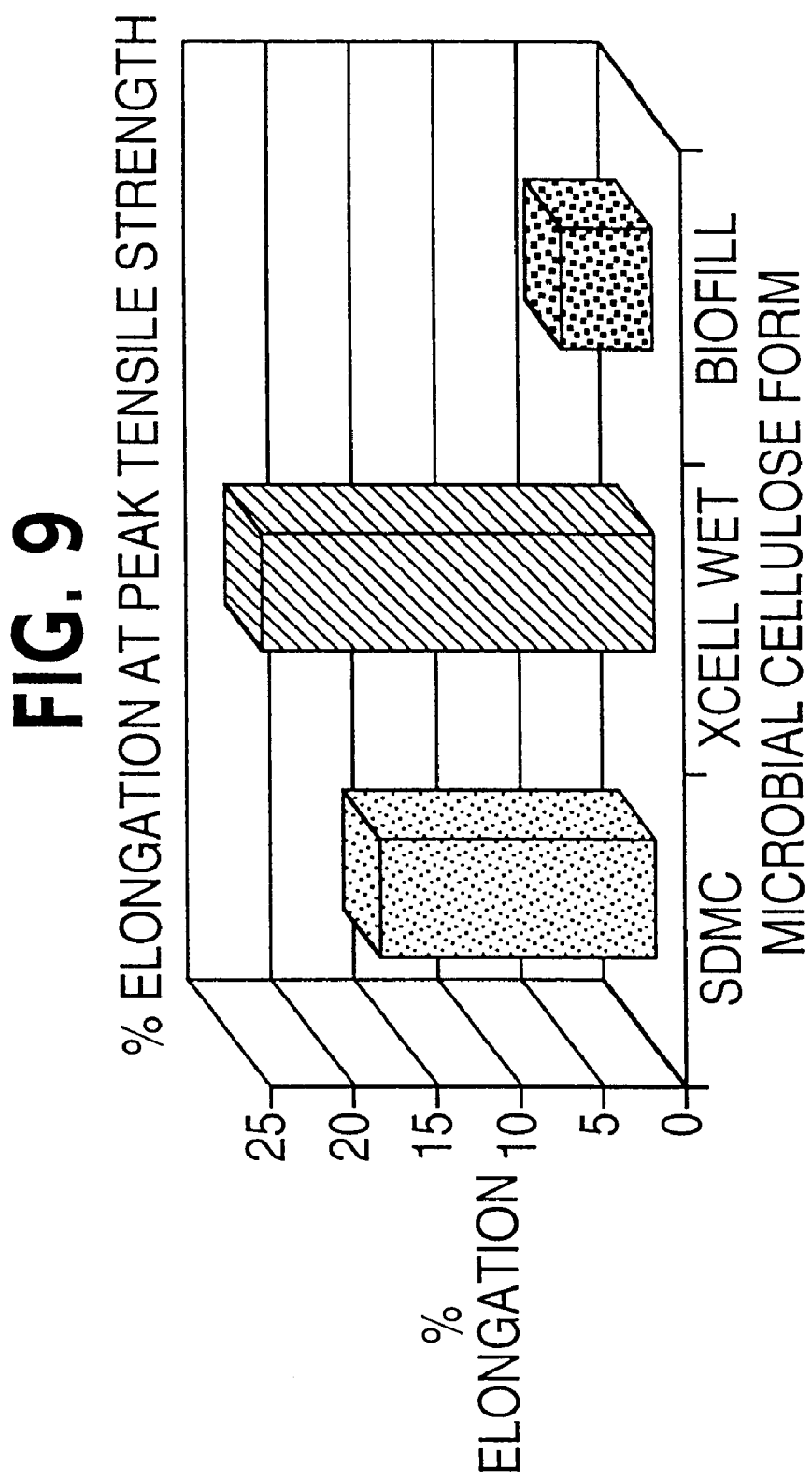
FIG. 9 shows mechanical strength in a graph which demonstrates % elongation of wet cellulose (XCELL®) is greater than solvent dehydrated microbially derived cellulose, which indicates that wet cellulose will stretch during implant, healing and function.
Figure 10:
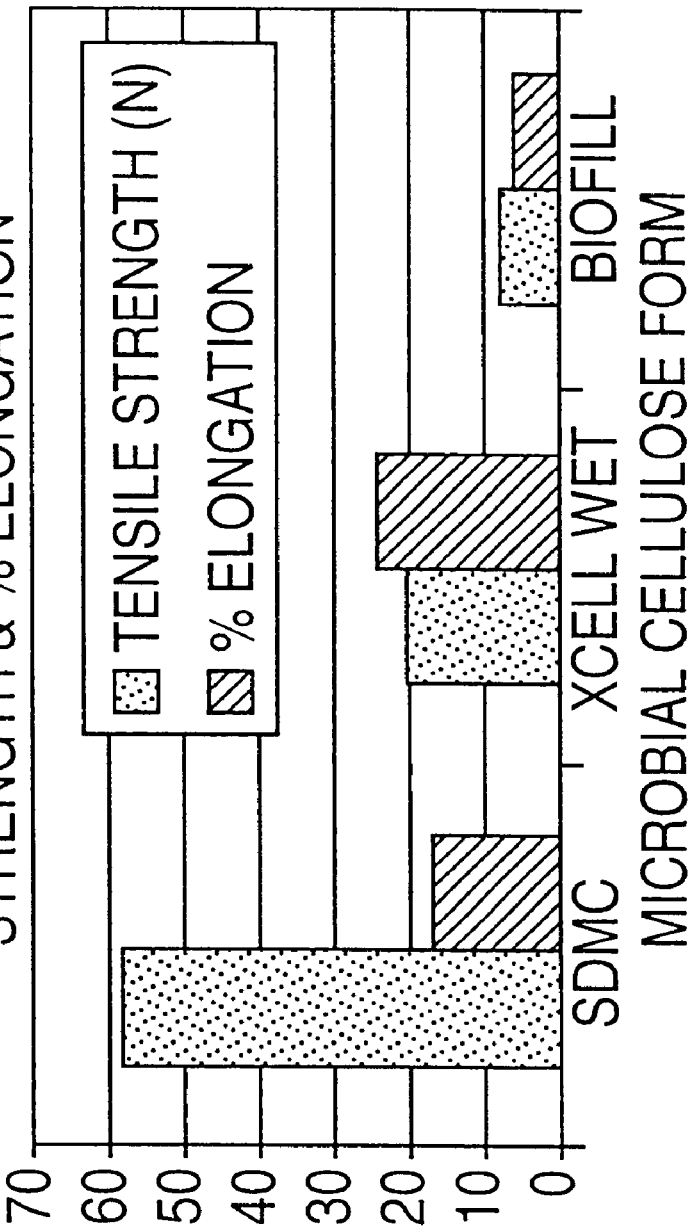
FIG. 10 shows mechanical strength in a graph which shows the superior tensile strength and % elongation of solvent dehydrated microbially derived cellulose when compared to wet cellulose (XCELL®) and air-dried cellulose (BIOFILL™).

Comparison of Mechanical Properties of the Solvent Dehydrated Microbially-Derived Cellulose to Wet Microbially-Derived Cellulose and Commercial Products A general mechanical strength analysis of various microbially derived cellulose materials was performed for demonstration of various degrees of tensile strength, % elongation and suture retention. Table 3 and FIGS. 8, 9 and 10 show the comparison of Solvent Dehydrated Microbially-Derived Cellulose (SDMC) to wet microbially derived cellulose (XYLOS™ XCELL® Wound Dressing) and to air-dried, stretched microbially derived cellulose BIOFILL™ (BioFill Productos Biotechnologicos, Curritiba, Parana, Brazil.) The XCELL® Wound Dressings and BIOFILL™ were cut into 1×4 cm strips and underwent testing as in Example 3. The XCELL® Wound Dressing is a sterile *A. xylinum* derived cellulose-water hydrogel film comprised of approximately 90 to 95% water and approximately 5 to 10% cellulose. BIOFILL™ is also synthesized from *A. xylinum* and is processed to a film that is air-dried during stretching.

Table 3 shows results of averaged test data for Tensile Strength, % Elongation and Suture Pull-out for Solvent Dehydrated Microbial Cellulose, XCELL® Wound Dressing (wet cellulose) and BIOFILL™ cellulose. SDMC demonstrated superior tensile strength (N) when compared to wet microbial cellulose (XCELL®) by 185% and to air-dried BIOFILL™ by 649%. Tensile strength is important during surgical handling, insertion, the healing process, and implant function.

Wet microbial cellulose (XCELL®) demonstrated greater % Elongation by 40% when compared to the SDMC. This indicates that the wet cellulose has greater "stretch", a non-desirable characteristic when implant indications are for bladder neck suspension, pelvic floor reconstruction, hernia repair, etc.

TABLE 3

|  | SDMC | XCELL Wet | BIOFILL ™ |
|---|---|---|---|
| Tensile Strength (N) | 57.94 | 20.29 | 7.74 |
| % Elongation | 16.78 | 23.97 | 5.77 |
| Suture Pull-Out | 8.03 | 6.10 | N/A* |

*BIOFILL material did not hold suture, tore during 1N pre-load (0.2N)

As shown in FIG. 8 SDMC at 57.94N is superior in tensile strength to wet cellulose (XCELL®) at 20.29N and air-dried cellulose (BIOFILL™) at 7.74N.

Furthermore, FIG. 9 shows that % Elongation of wet cellulose (XCELL®) is greater than SDMC, which indicates that wet cellulose will stretch during implant, healing and function.

The air-dried cellulose (BIOFILL™) had minimal extensibility and was extremely difficult to handle during mechanical testing. After rehydration, the air-dried cellulose (BIOFILL™) became transparent, difficult to handle due to rolling and puckering during insertion into the grip clamps, and several pieces broke prior to the pulling process due to immediate drying during ambient working conditions.

In addition, FIG. 10 demonstrates the superior tensile strength and % elongation of SDMC, as compared to wet cellulose (XCELL®) and air-dried cellulose (BIOFILL™).

Figure 11:
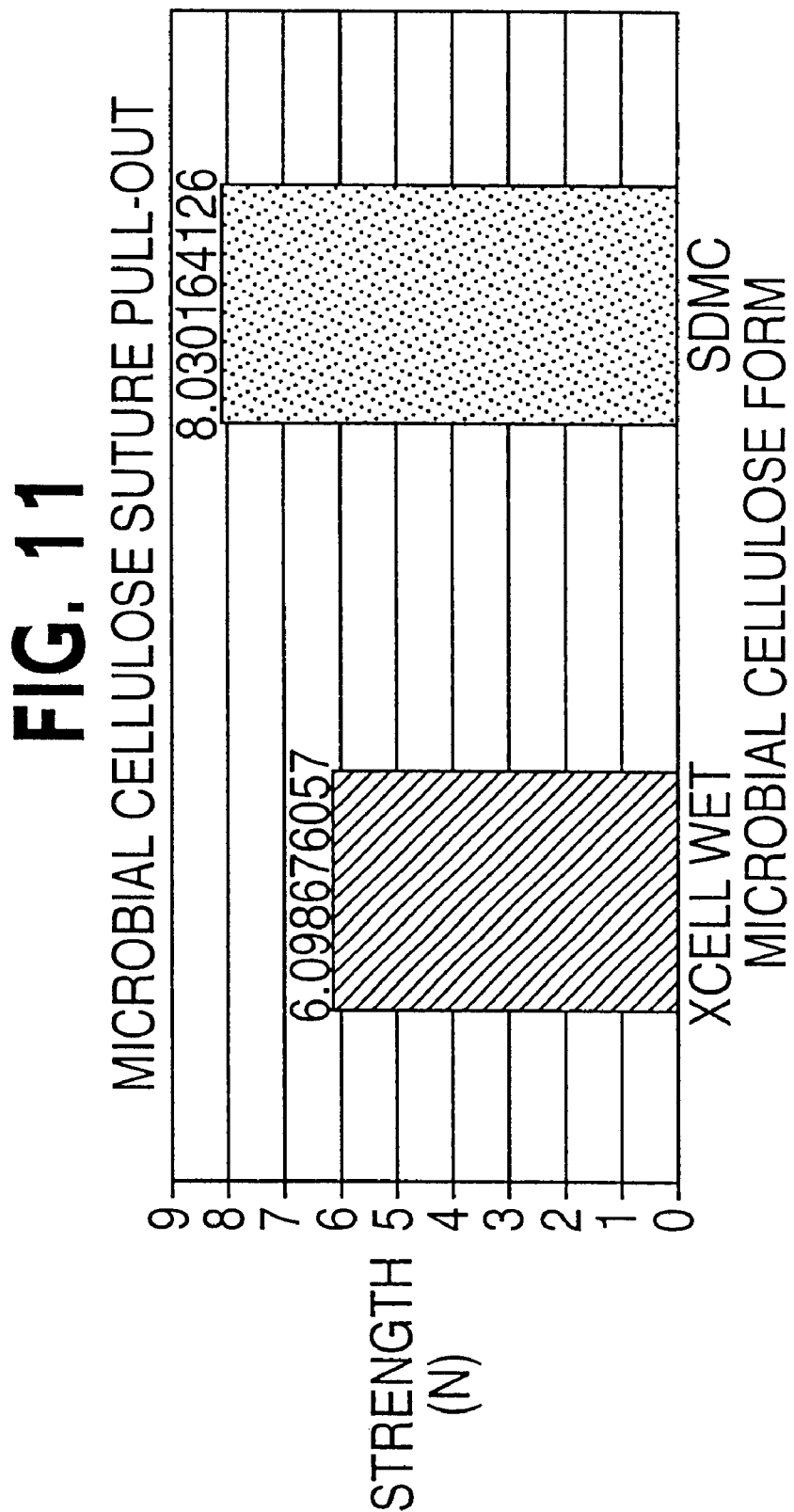
FIG. 11 shows suture retention in a graph presents the results of comparative suture retention.

With respect to suture pullout, FIG. 11 presents the results of suture retention. It is important to note that that the air-dried cellulose (BIOFILL™) is not present because of the inability of the BIOFILL™ material to accept a suture. The SDMC was capable of holding sutures 32% greater during the testing process than the wet cellulose (XCELL®).

Figure 12:
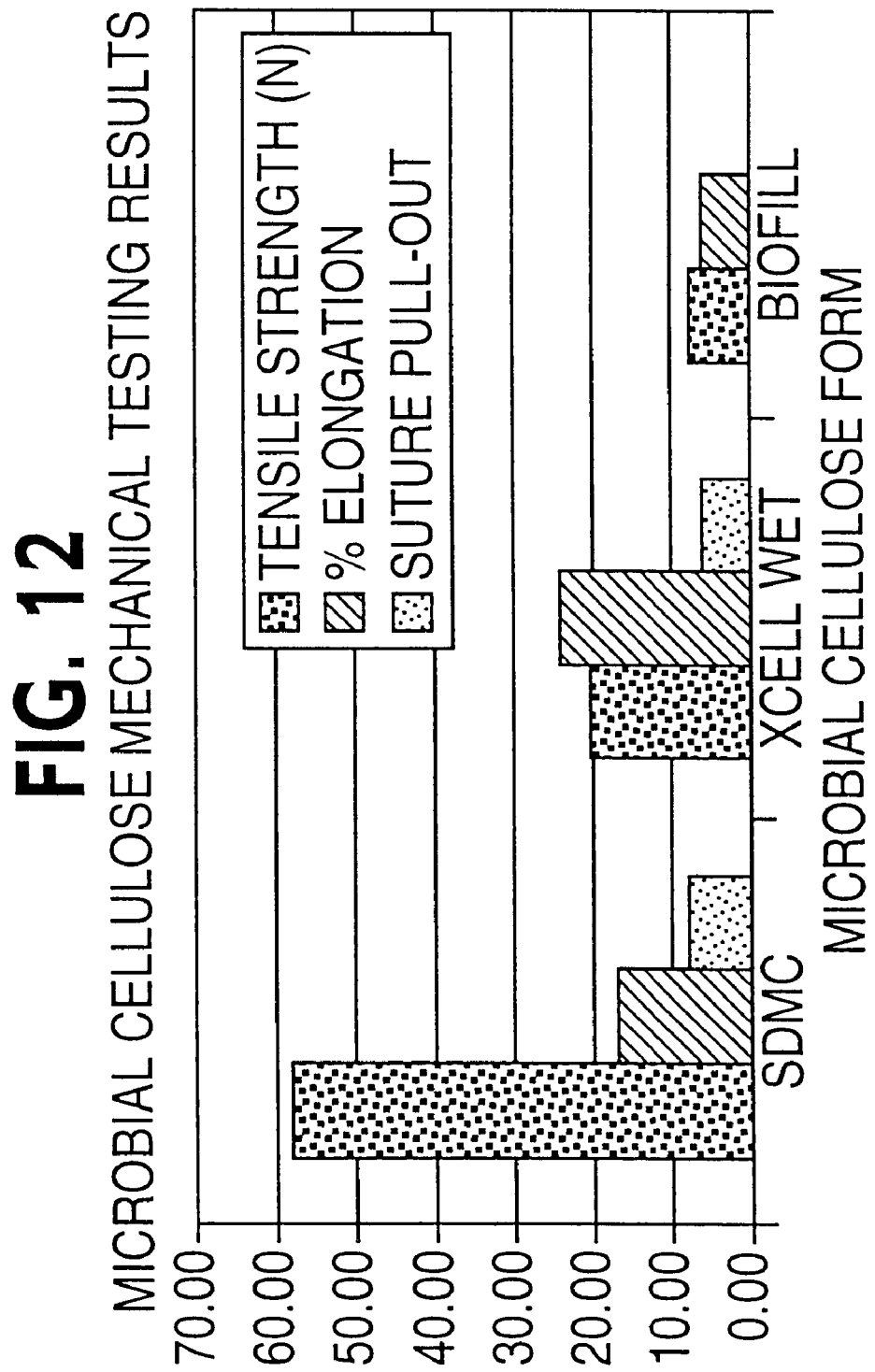
FIG. 12 shows mechanical strength and suture retention of a compilation of mechanical and suture retention testing performed on the three types of microbially derived cellulose materials.

Lastly, FIG. 12 provides a compilation of all mechanical testing performed on the three types of microbially derived cellulose materials.

The present inventive cellulose material as well as the wet cellulose (XCELL®) and air-dried cellulose (BIOFILL™) were derived from *Acetobacter xylinum*. The results show clear differences in the mechanical properties between the materials that were produced by different processes. It is believed that the difference in mechanical properties is due to the preparation process of the present inventive microbially-derived cellulose. Solvent dehydration of cellulose films allows for better control of the resulting film properties, therefore, it is expected that the present invention is capable of performing as an implantable material with better results than previous implantation materials.

EXAMPLE 6

Biocompatibility

A single extract of the test article was prepared using single strength Minimum Essential Medium supplemented with 5% serum and 2% antibiotics (1×MEM). This test extract was placed onto three separate confluent monolayers of L-929 mouse fibroblast cells propagated in 5% $CO_2$.

Three separate monolayers were prepared for the reagent control, negative control and for the positive control. All monolayers were incubated at 37° C. in the presence of 5% $CO_2$ for 48 hours. The monolayer in the test, reagent control, negative control and positive control wells was examined microscopically at 48 hours to determine any change in cell morphology.

Under the conditions of the study, the 1×MEM test extracts showed no evidence of causing cell lysis or toxicity. The 1×MEM test extract met the requirements of the test since the grade was less than a grade 2 (mild reactivity). The reagent control, negative control and the positive control performed as anticipated. The solvent dehydrated microbially-derived cellulose is therefore not toxic to mammalian cells and may be considered biocompatible for human implantation.

EXAMPLE 7

SEM Comparison

Figure 13:
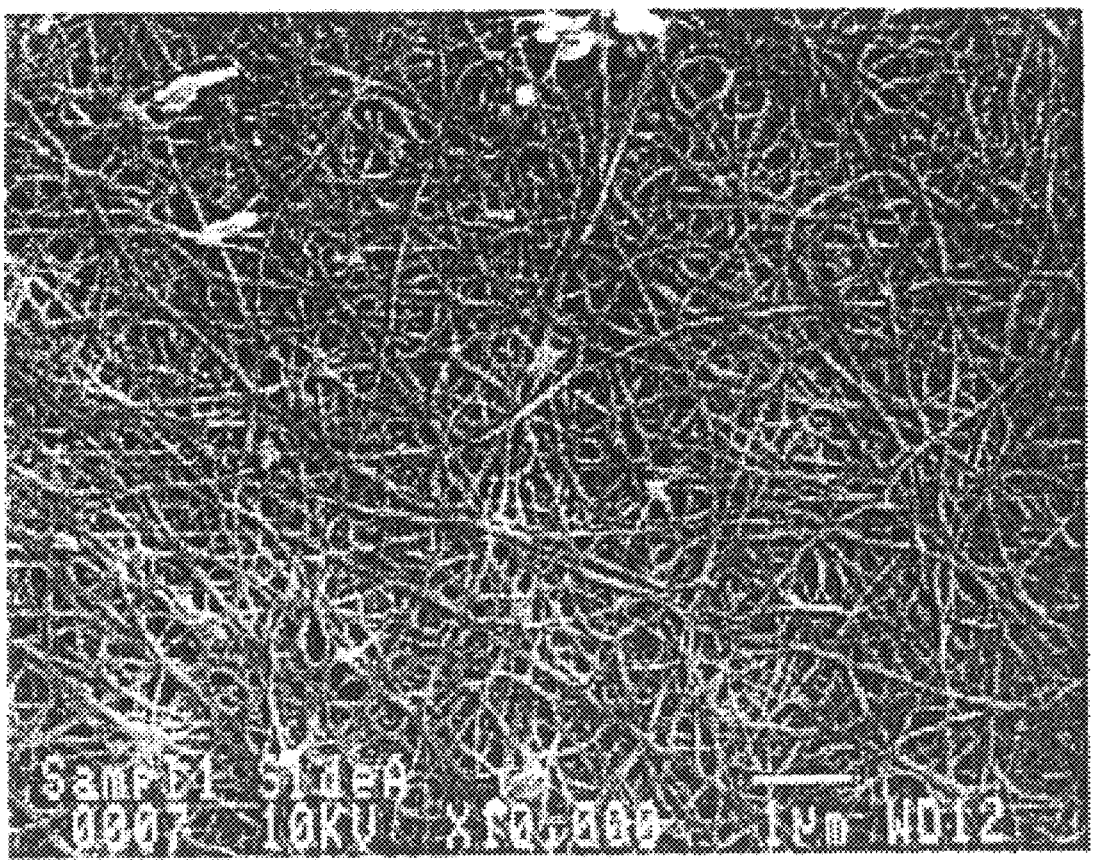
FIG. 13 shows an electromicrograph of the magnified surface (10,000 times) of SDMC.
Figure 14:
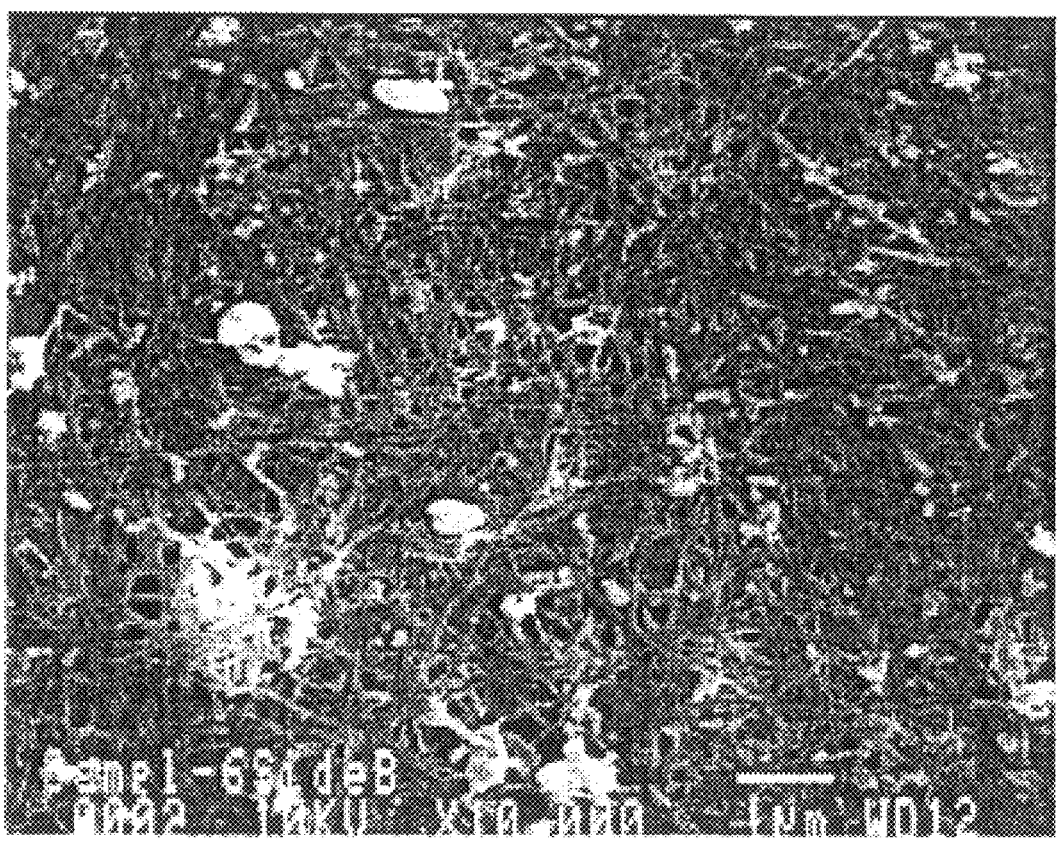
FIG. 14 shows an electromicrograph of the magnified surface (10,000 times) of XCELL®.
Figure 15:
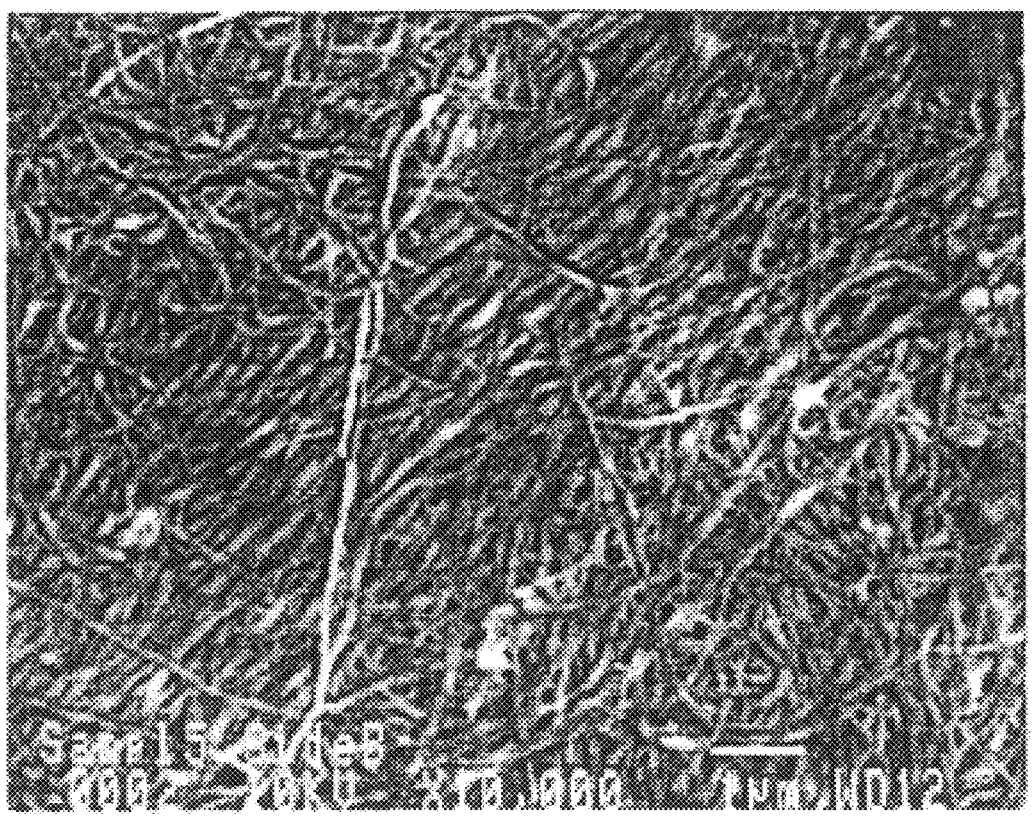
FIG. 15 shows an electromicrograph of the magnified surface (10,000 times) of BIOFILL™.
Figure 16:
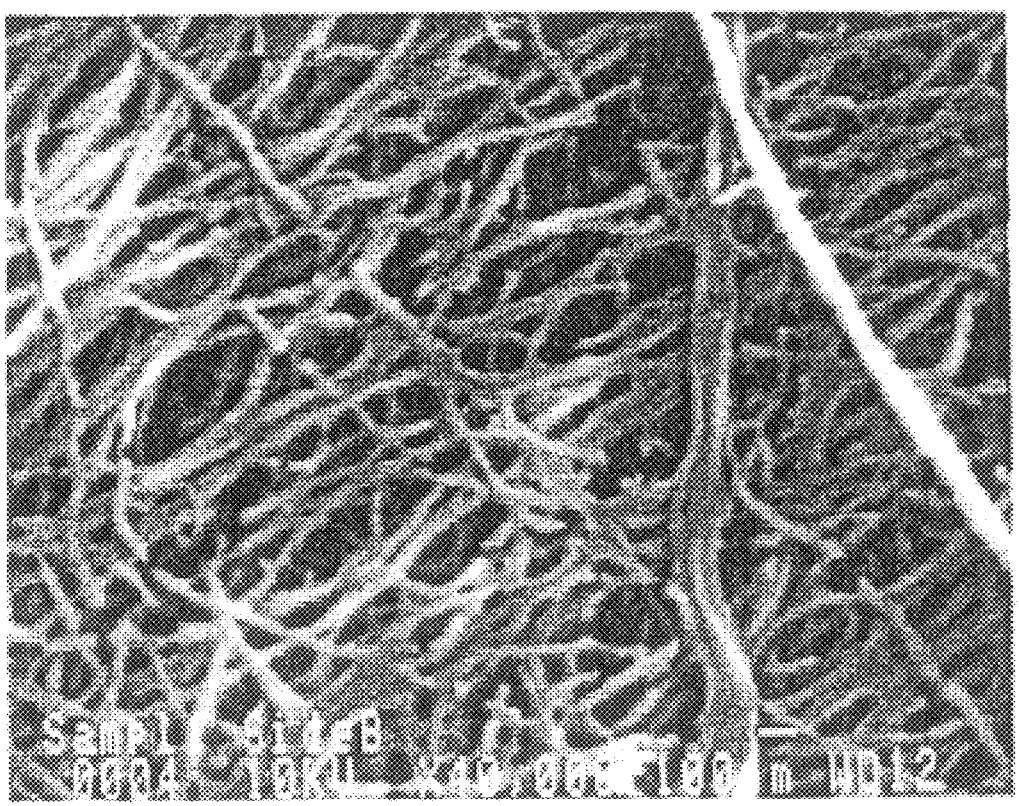
FIG. 16 shows an electromicrograph of the magnified surface (40,000 times) of SDMC.
Figure 17:
FIG. 17 shows an electromicrograph of the magnified surface (40,000 times) of XCELL®.
Figure 18:
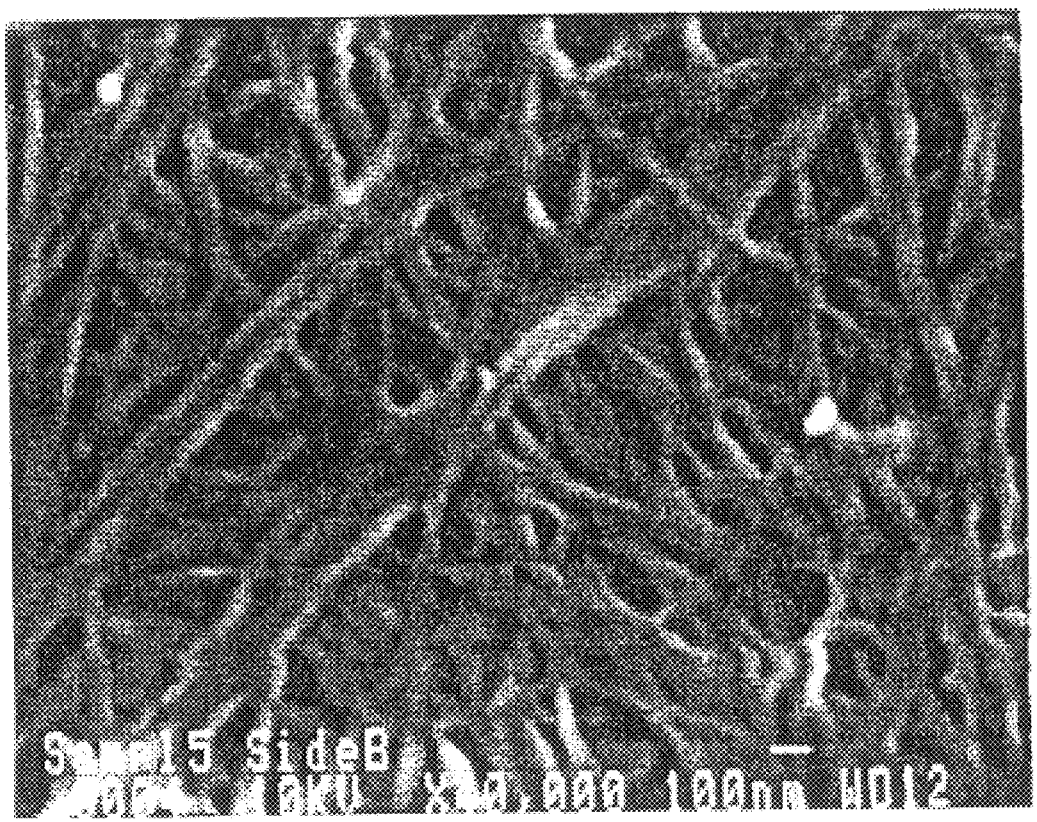
FIG. 18 shows an electromicrograph of the magnified surface (40,000 times) of BIOFILL™.

A microscopic comparison of the three microbial cellulose materials, namely, BIOFILL™, XCELL® and solvent dehydrated microbially derived cellulose (SDMC) was performed using a scanning electron microscope (SEM). Two pictures of the surface of each material were taken at 10,000 and 40,000 times magnifications. FIGS. 13–15 shows the magnified surface of the three materials at 10,000 times magnification with SDMC (FIG. 13); XCELL® (FIG. 14) and BIOFILL™ (FIG. 15). It was observed from the electron micrographs that there is marked difference in the final surface structure of the solvent dehydrated samples of the present invention as compared to the air dried samples of the XCELL® and BIOFILL™ materials. The SDMC surface (FIG. 13) presents a more defined micro-fibril structure and the individual fibers are distinctly preserved by the drying process. Both air-dried XCELL® and BIOFILL™ (FIGS. 14 and 15) surfaces show considerable inter-fibril interaction as evidenced by the aggregation of the individual fibers. The SDMC surface also appears to be more porous as compared to the other two samples. Further evidence of the SDMC's more open structure and minimized inter-fibril interaction can be seen in FIG. 16, which shows the micro-fibril structure at 40,000 times magnification as compared to XCELL® and BIOFILL™, (FIGS. 17 and 18), respectively.

This unique and unexpected microstructure of the SDMC samples can be attributed to the use of solvents, which exert less inter-fibril surface tension than water during the drying process. It is a well-known phenomenon that when the liquid between fibrils evaporates, it has tendency to pull the two adjacent fibers together and this pulling action is called surface tension. Thus, because of the lowered surface tension encountered during the drying process, the SDMC samples showed more preserved micro-fibril structure and less binding between the individual fibers. The more defined micro-fibril structure of the SDMC sheets is particularly important to the intended application of these materials as implantable medical devices. For example, the less inter-fiber binding brought about by the solvent dehydration process produces a sheet with a finer fibril structure which has more surface area available for interaction as compared to the densified air dried samples. The porosity of the resulting sheet can also be important for a medical implant especially if fluid/mass transfer and cellular infiltration is desired. Therefore, the solvent dehydration procedure described in this patent provides some control of the resulting dehydrated material, thus, allowing the fabrication of various materials with different fiber density and porosity enabling the use of microbial cellulose in a wide range of medical applications including implantable surgical mesh and tissue substitutes.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims and their equivalents. It will be understood that the solvent dehydrated microbial cellulose material disclosed herein may be used in most applications for which known cellulose items are used.

We claim:

1. A method for preparing an implantable material for medical and surgical applications comprising the steps of:
   a) providing a microbially-derived cellulose;
   b) treating said microbially-derived cellulose to render said cellulose non-pyrogenic;
   c) dehydrating said microbially-derived cellulose in a continuous manner by applying a water-miscible organic solvent selected from the group consisting of methanol, ethanol, propanol, isopropanol, acetone and mixtures thereof to said microbially-derived cellulose; and
   d) subsequently removing said solvent.

2. The method according to claim 1, wherein the microbially-derived cellulose is produced by the bacteria *Acetobacter xylinum*.

3. The method according to claim 1, wherein treating said microbially-derived cellulose comprises using a chemical wash.

4. The method according to claim 3, wherein the chemical wash comprises sodium hydroxide.

5. The method according to claim 4, wherein the sodium hydroxide concentration is from about 0.1M to about 4M.

6. The method according to claim 1, where in the solvent is acetone.

7. The method according to claim 1, wherein said solvent is removed at ambient or atmospheric pressure.

8. The method according to claim 7, wherein said solvent is removed at about 25° C. to about 50° C.

9. The method according to claim 7, wherein said solvent is removed over about 1–24 hours.

10. A method of preserving microbially-derived cellulose for use as a human implantable device comprising
    a) contacting said microbially-derived cellulose with a water-miscible organic solvent selected from the group consisting of methanol, ethanol, propanol, isopropanol, acetone and mixtures thereof thereby dehydrating said microbially-derived cellulose and
    b) removing said solvent at ambient or atmospheric pressure.

11. A kit comprising
    a) a microbially-derived cellulose, prepared by the method of claim 10, for use as an implantable material and
    b) a moisture proof package containing said microbially-derived cellulose.

12. An in vivo implantable material comprising a microbially-derived cellulose, prepared by the method of claim 10, wherein said microbially derived cellulose is non-pyrogenic.

13. The in vivo implantable material of claim 12, wherein said microbially-derived cellulose is sterilized by gamma irradiation.

14. A method of tissue augmentation comprising
    a) providing an implantable material which comprises a microbially derived cellulose, prepared by the method of claim 10 and
    b) implanting said material into a subject in need thereof.

15. The method according to claim 1, wherein the material comprises a tissue substitute.

16. The method according to claim 1, wherein the material comprises an implantable bulking agent.

17. The method according to claim 1, wherein the material comprises an implantable surgical mesh.

* * * * *